Figure 1:
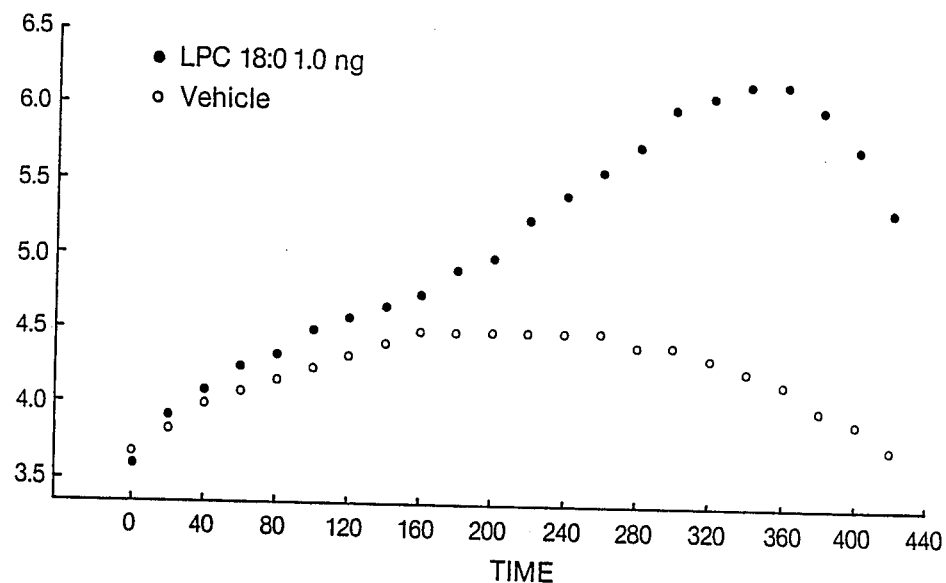

United States Patent [19]

Buckalew, Jr. et al.

[11] Patent Number: 4,746,652

[45] Date of Patent: May 24, 1988

[54] METHOD OF INDUCING DIURESIS WITH LYSOPHOSPHOLIPIDS

[75] Inventors: Vardaman M. Buckalew, Jr.; Albert L. Rauch, both of Winston-Salem, N.C.

[73] Assignee: Wake Forest University, Winston-Salem, N.C.

[21] Appl. No.: 932,462

[22] Filed: Nov. 18, 1986

[51] Int. Cl.$^4$ .......................................... A61K 31/685
[52] U.S. Cl. ................................................ 514/77
[58] Field of Search .................................. 514/77, 114

[56] References Cited

U.S. PATENT DOCUMENTS 3,705,213 12/1972 Pfeiffer et al. ...................... 558/169
4,552,869 11/1985 Lautenschlager et al. ............ 514/77

FOREIGN PATENT DOCUMENTS 53-133617 11/1978 Japan.

OTHER PUBLICATIONS

M. Tamura and T. Inagami, *Federation Proceedings* 45, 523, No. 2151 (1986).
H. Tsukatani, S. Yamada, K. Fukuzawa, C. Hamaguchi, *Communications, J. Pharm. Pharmacol.* 31, 110 (1979).
Mizuo Miyazaki and Kenjiro Yamamoto, *Proceedings of the Society for Experimental Biology and Medicine* 155, 468 (1977).
Ralph A. Kelly, Donald S. O'Hara, Mitzy L. Canessa, William E. Mitch and Thomas W. Smith, *J. Biol. Chem.* 260, 11396 (1985).
Tsukatani, H., Hypotensive Phospholipid Containing Choline is Obtained from Animal Tissue or Body Fluid (1978), (English Abstract and Foreign Language Document).
Vardaman M. Buckalew, Jr. and Kenneth A. Gruber, *Ann. Rev. Physiol*, 46, 343 (1984).
Vardaman M. Buckalew, Jr. and Kenneth A. Gruber, Natriuretic Hormone, in: The Kidney in Liver Disease (M. Epstein, 2nd Ed. 1983).

*Primary Examiner*—Allen J. Robinson
*Attorney, Agent, or Firm*—Bell, Seltzer, Park & Gibson

[57] ABSTRACT

Lysophospholipids are used to induce diuresis in a subject by administering them in a dose effective to increase the renal excretion of sodium. Exemplary compounds useful in this method include steroyl-lysophosphatidylcholine and steroyl-lysophosphatidylethanolamine.

7 Claims, 1 Drawing Sheet

METHOD OF INDUCING DIURESIS WITH LYSOPHOSPHOLIPIDS

FIELD OF THE INVENTION

The present invention relates to methods of inducing diuresis by administering lysophospholipids in amounts effective to increase renal sodium excretion.

BACKGROUND OF THE INVENTION

Control of sodium excretion by the kidneys is important in maintaining the correct amount of fluid and salt in the body. In some people, retention of salt and fluid causes hypertension. In others, it causes swelling of the legs, face, hands, abdomen (ascites), etc. Excess fluid can also collect in the lungs, causing difficulty in breathing.

Sodium and fluid retention can be caused by a number of different conditions or abnormalities, including heart, liver and kidney failure. Some patients retain fluid for reasons which are not entirely clear.

Numerous drugs which aid the kidneys in excreting fluid, referred to as diuretics, are currently available. These diuretics operate in different ways, and are suitable for different conditions. Some, such as the Loop of Henle diuretics (i.e., Furosemide, Ethacrynic Acid, and Bumetanide) (also called "high-ceiling" diuretics), operate by increasing the renal excretion of sodium (by inducing natriuresis), with increased fluid excretion following the increased sodium excretion. Such diuretics are among the few diuretics available that have an effect on patients with impaired renal function. See generally *Goodman and Gilman's The Pharmacological Basis of Therapeutics* 896–900 (A. G. Gilman, L. S. Goodman, T. W. Rall, and F. Murad 7th Ed. 1985) (hereinafter "Goodman and Gilman"); *Veterinary Pharmacology and Therapeutics* 492–98 (N. H. Booth and L. E. McDonald 5th Ed. 1982).

Diuretics are useful in veterinary medicine, as well as for treating humans. Animals treated with diuretics include, for example, dogs, cats, horses, and dairy cattle. These agents are administered to animals to treat edema, pulmonary congestion, ascites, hydrothorax, pulmonary edema, or any pathologic accumulation of noninflammatory fluid. *Veterinary Pharmacology and Therapeutics*, supra. In any case, all diuretics have undesirable side effects, and there is ongoing interest in developing new and better products in this field.

Because the control of sodium excretion is of such importance, there has been considerable interest in the identification of endogenous natriuretic factors which might play a role in physiology and pathophysiology. A number of endogenous natriuretic compounds have been identified. Chief among them are the prostaglandins, dopamine, fragments of the pro-opiomelanocortin molecule, and vasopressin. Recently, a family of peptides synthesized by the cardiac atria have been identified: these are referred to as atrial natriuretic factors. These peptides are released into the circulation following the ingestion of sodium, and appear to function as a natriuretic hormone. See also V. M. Buckalew and K. M. Gruber, Natriuretic Hormone, 46 *Ann. Rev. Physiol.* 343 (1984).

The possibility that a plasma lipid (or lipids) might function as a natriuretic hormone has only recently begun to emerge. Kelly et al., 260 *J. Biol. Chem.* 11,396 (1985), and Tamura et al., 26 *J. Biol. Chem.* 9672 (1985), have recently demonstrated that some of the digitalis-like activity in plasma is accounted for by a variety of lipids. Applicants' research into the mechanisms controlling sodium excretion has for the first time revealed that lysophospholipids are natriuretic.

DESCRIPTION OF THE INVENTION

The present invention is a method of inducing diuresis in a human or animal subject. The method comprises administering to the subject a compound of the formula

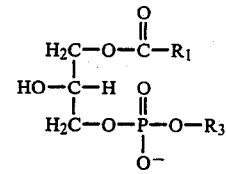

wherein $R_1$ is an alkyl group having from 12 to 24 carbon atoms, or an alkenyl group having from 12 to 24 carbon atoms with not more than four carbon-carbon double bonds, and wherein $R_3$ is selected from the class consisting of choline, ethanolamine, and serine. Pharmaceutically acceptable salts of these compounds are also used in this method. The compound is administered in an amount effective to increase the subject's renal excretion of sodium. Exemplary lysophospholipids useful in practicing the present invention include the following: 1-acyl(lauroyl)-sn-glycero-phosphorylcholine; 1-acyl(myristoyl)-sn-glycero-phosphorylcholine; 1-acyl(palmitoyl)-sn-glycero-phosphorylcholine; 1-acyl(steroyl)-sn-glycero-phosphorylcholine; 1-acyl(elaidoyl)-sn-glycero-phosphorylcholine; 1-acyl(oleoyl)-sn-glycero-phosphorylcholine; 1-acyl(linoleoyl)-sn-glycero-phosphorylcholine; 1-acyl(linolenoyl)-sn-glycero-phosphorylcholine; 1-acyl(arachidonyl)-sn-glycero-phosphorylcholine; and 1-acyl(phytanoyl)-sn-glycero-phosphorylcholine. Analogous series of compounds, in which serine or ethanolamine replace choline at the $R_3$ position, are also exemplary of compounds useful for practicing the present invention. As explained below, choline and ethanolamine are the preferred substituents at the $R_3$ position. As also explained below, $R_1$ is preferably a long chain alkyl group with from 14 to 20 carbons. $R_1$ is most preferably a straight chain alkyl group. These are known compounds which can be prepared in the lab, see, e.g., M. Miyazaki and K. Yamamoto, 155 *Proc. Soc. Exp. Biol. Med.* 468, 468 (1977), or obtained from commercial sources such as Serdary Research Labs, Inc., P.O. Box 355, Port Huron, Mich. 48060-0355.

These compounds can be administered a variety of ways, including orally, by subcutaneous injection, and by intravenous injection, with intravenous injection preferred. They can be administered to induce diuresis in human subjects and in animal subjects. Exemplary animal subjects include, for example, dogs, cats, horses, and dairy cattle. These compounds are highly active in inducing diuresis, and are preferably administered to the subject in amounts of from about 1.0 picomoles to about 10 nanomoles per kilogram of subject weight, or more preferably in an amount of from about 1.0 picomoles to about 500 picomoles per kilogram of subject weight. In addition, these compounds have a long-lasting action, and are preferably administered to subjects at intervals of not less than two hours, and more preferably not less than four hours, between administrations. This highly desirable long-lasting action contrasts with the brevity of action of other Loop of Henle diuretics. *Goodman and Gilman, supra* at 896. These compounds can be administered to subjects in need of a treatment for inducing diuresis for any of the reasons stated in the background section above.

These compounds can be administered to subjects in the form of their pharmaceutically acceptable salts. Pharmaceutically acceptable salts are salts that retain the desired biological activity of the parent compound and do not impart any undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acids, naphthalenedisulfonic acids, polygalacturonic acid, and the like; (b) salts with polyvalent metal cations such as zinc, calcium, bismuth, barium, magnesium, aluminum, copper, cobalt, nickel, cadmium, and the like; or with an organic cation formed from, N, N'-dibenzylethylenediamine or ethylenediamine; or (c) combinations, of (a) and (b), e.g. a zinc tannate salt, and the like.

While specific compounds useful for practicing the present invention have been described above, the information set forth herein also demonstrates that minor variations can be made to these compounds to make still other compounds useful for increasing renal sodium excretion. For example, the different $R_1$ groups and the different $R_3$ groups disclosed herein indicate that additional minor changes to these substituents can be made to produce compounds useful for inducing diuresis by increasing renal sodium excretion.

The following specific examples are provided to further illustrate the invention.

EXAMPLE 1

The effect of LPC on sodium excretion in the rat was determined by modification of a previously described method, Gruber et al., 6 Hypertension 468 (1984). 1-acyl(steroyl)-sn-glycero-phosphorylcholine (steroyl-LPC) (Serdary Research Laboratories) was dissolved at a concentration of 0.27 nanomolar in 75 millimolar NaCl by heating to 37° C. for five minutes and vortexing. Male Sprague Dawley rats weighing 140-180 grams were anesthetized with pentobarbital (50 milligrams/kilogram) intraperitoneally and femoral vein (PE 50), bladder (PE 160) and trachea (PE 240) were cannulated. A continuous infusion of 75 millimolar NaCl containing pentobarbital was given throughout the procedure at 100 microliters/minute. Pentobarbital was given at a rate of 0.12 milligrams/100 grams body weight/minute for the first 100 minutes, and at 0.35 milligrams/100 grams body weight/minute for the remainder of the procedure. Rectal temperature was maintained at 37°-39° C. by a heating pad. When a steady state baseline sodium excretion had been obtained, usually about two hours after induction of anesthesia, 0.7 milliliters of the LPC solution (2.0 picomoles) was injected intravenously over seven minutes. Control rats received 0.7 milliliters of 75 millimolar NaCl. Urine was collected every 20 minutes in graduated cylinders, the volume measured and the sodium concentration determined by flame photometry.

The effect of 1.0 ng bolus injection of lysophosphatidyl choline (LPC) intravenously in the anesthetized rat assay is shown in FIG. 1. LPC is given at time zero when a steady state baseline of renal sodium excretion (UNaV) had been obtained. The effect of injecting a similar volume of the vehicle for LPC (75 mM saline) is also shown. The data are presented as the best fit polynomial with the following configuration:

$$UNaV = 3.61 + 0.0174t - 1.432 \times 10^{-4}t^2 + 6.357 \times 10^{-7}t^3 - 8.822 \times 10^{-10}t^4 (n=6; r=0.899)$$

for LPC 1.0 ng:

$$UNaV = 3.69 + 0.00767t - 1.79 \times 10^{-5}t^2 (n=6)$$

for vehicle. Analysis of variance shows the configuration of the two curves to be significantly different ($p < 0.005$).

The natriuretic effect of LPC is slow in onset, overlapping with the effect of the vehicle until approximately 160-200 minutes after injection. Peak effect occurs approximately six hours after injection (360 minutes), and is still detectable seven hours (420 minutes) after injection. This figure demonstrates that LPC is extremely effective at increasing the renal excretion of sodium at a very low dosage over a long period of time.

EXAMPLES 2-6

The procedure described in Example 1 above was repeated with (1) 1-alkyl(palmitoyl)-sn-glycero-3 phosphorylcholine (lyso-platlet activating factor or LPAF); (2) 1-acyl(steroyl)-sn-glycero-3 phosphate (lysophosphatidic acid); (3) 1-acyl(steroyl)-sn-glycero-3 phosphatidylethanolamine (lyso-phosphatidylethanolamine); (4) 1-acyl(steroyl)-sn-glycero-3 phosphatidylserine (steroyl-lyso-phosphatidylserine); and (5) 1-acyl(linoleoyl)-sn-glycero-3 phosphorylcholine (linoleoyl-lysophosphatidyl choline). The first of these compounds did not have significant activity in increasing renal sodium excretion; the second and fifth of these compounds acted to a lesser extent than steroyl-LPC; and the third and fourth of these compounds increased renal sodium excretion to the same extent as steroyl-LPC. These examples demonstrate that a range of these compounds have natriuretic activity, and that the structures preferred for obtaining maximum activity include (1) an acyl linkage to the $R_1$ alkyl group on the first carbon of the glycerol backbone, (2) a long chain, saturated fatty acid on the first carbon of the glycerol backbone, and (3) a choline or ethanolamine group as $R_3$ on the phosphoryl group.

Figure 2:
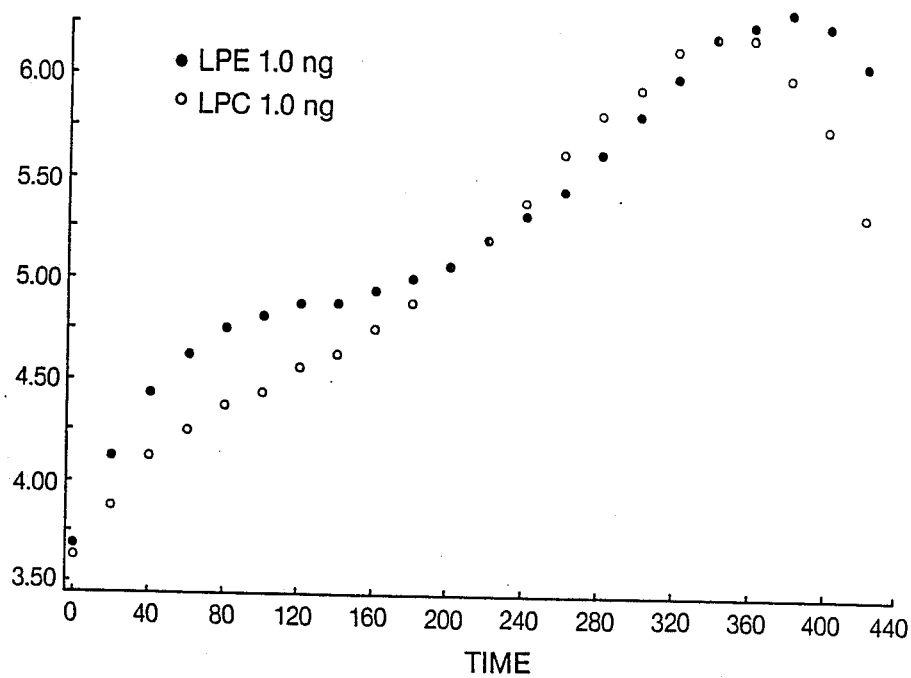

In FIG. 2, the effect of 1.0 ng bolus injection of lysophosphatidylethanolamine (LPE) is compared to that of LPC on renal sodium excretion. Data are presented as in FIG. 1. The polynomial for the response of LPE is as follows:

$$UNaV = 3.674 + 0.0267t - 2.231 \times 10^{-4}t^2 + 8.148 \times 10^{-7}t^3 - 9.59 \times 10^{-10}t^4 (n=6; r=0.939).$$

Analysis of variance shows no difference in the configuration of the polynomial for LPC and LPE.

The foregoing examples have been provided to illustrate the present invention. While specific terms are employed, they are used in a generic, descriptive sense only and not for purposes of limitation, the scope of the That which is claimed is:

1. A method of inducing diuresis in a human or animal subject in need of said treatment comprising administering to the subject in an amount effective to increase the subject's renal excretion of sodium, a compound or a pharmaceutically acceptable salt thereof, said compound being of the formula

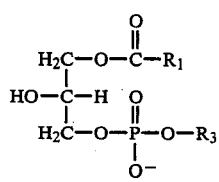

wherein $R_1$ is an alkyl group having from 12 to 24 carbon atoms, or an alkenyl group having from 12 to 24 carbon atoms with not more than four carbon-carbon double bonds, and wherein $R_3$ is selected from the class consisting of $-CH_2CH_2N^+(CH_3)_3$, $-CH_2CH_2NH_3^+$, and $-CH_2CHNH_3^+COO-$.

2. A method according to claim 1, wherein said compound is administered by intravenous injection.

3. A method according to claim 1, wherein said compound is administered in an amount of from about 1.0 picomole to about 10 nanomole per kilogram of subject weight.

4. A method according to claim 1; wherein $R_3$ is selected from the group consisting of $-CH_2CH_2N^+(CH_3)_3$ and $-CH_2CH_2NH_3^+$.

5. A method according to claim 1, wherein $R_1$ is a long chain alkyl group having from 14 to 20 carbon atoms.

6. A method according to claim 1, wherein said compound is administered to said subject at intervals of not less than two hours between administration.

7. A method of inducing diuresis in a human or animal subject in need of said treatment, comprising administering to the subject in an amount effective to increase the subject's renal excretion of sodium at intervals of not less than two hours between administration a compound or a pharmaceutically acceptable salt thereof, said compound being of the formula:

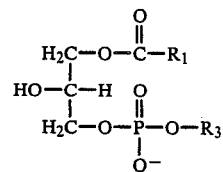

wherein $R_1$ is a long chain alkyl group having from 14 to 20 carbon atoms, and wherein $R_3$ is selected from the class consisting of $CH_2CH_2N^+(CH_3)_3$ and $-CH_2CH_2NH_3^+$.

* * * * *